United States Patent [19]
Zwislocki et al.

[11] Patent Number: 5,153,387
[45] Date of Patent: Oct. 6, 1992

[54] LAYERED EARPLUG

[75] Inventors: Jozef J. Zwislocki, Cazenovia; Richard B. Mitchell, Liverpool, both of N.Y.

[73] Assignee: Syracuse University, Syracuse, N.Y.

[21] Appl. No.: 636,194

[22] Filed: Dec. 31, 1990

[51] Int. Cl.5 ............................................. H04R 25/00
[52] U.S. Cl. .................................... 181/129; 181/130; 181/135
[58] Field of Search ............... 181/128, 129, 130, 135; 381/68.6, 69; 128/151, 152, 864, 867

[56] References Cited

U.S. PATENT DOCUMENTS

| Re. 29,487 | 12/1977 | Gardner | 128/152 |
|---|---|---|---|
| 262,775 | 1/1882 | Lilley | D8/402 |
| 263,022 | 2/1882 | Lilley | D8/402 |
| 1,148,849 | 8/1915 | Mallock . | |
| 2,246,736 | 8/1938 | Knudsen | 128/152 |
| 2,446,707 | 3/1945 | Leight | 127/152 |
| 2,538,339 | 9/1949 | Thomas | 128/151 |
| 3,097,643 | 8/1961 | Santi | 128/152 |
| 3,800,791 | 4/1974 | Visor | 128/152 X |
| 4,193,396 | 3/1980 | Wacker | 181/135 X |
| 4,340,129 | 7/1982 | Salyers | 181/200 |
| 4,344,425 | 8/1982 | Strauss | 128/152 |
| 4,344,621 | 8/1982 | Baker | 273/26 A |
| 4,434,794 | 3/1984 | Leight | 128/152 |
| 4,867,149 | 9/1989 | Falco | 128/864 |

Primary Examiner—L. T. Hix
Assistant Examiner—Khanh Dang
Attorney, Agent, or Firm—Wall and Roehrig

[57] ABSTRACT

A novel earplug comprising a stack of thin flexible plastic discs bonded together about a central hole and loose at the edges is formed with a central core or plug forming a nose or bumper and a handle tail. The configuration described permits easy insertion and removal from the ear and the multiple disc structure forms a barrier to the entry of acoustic noise into the ear canal.

19 Claims, 1 Drawing Sheet

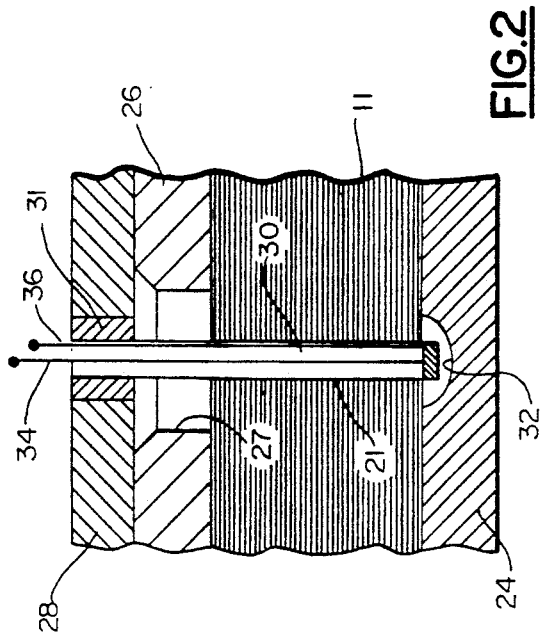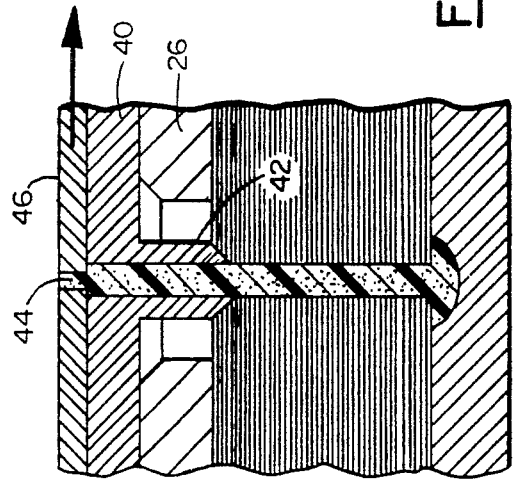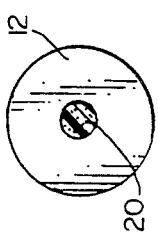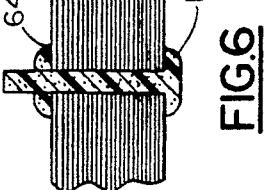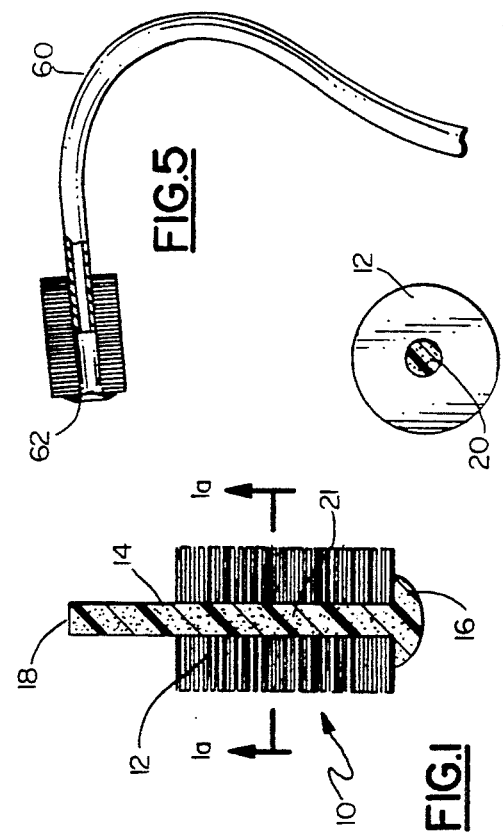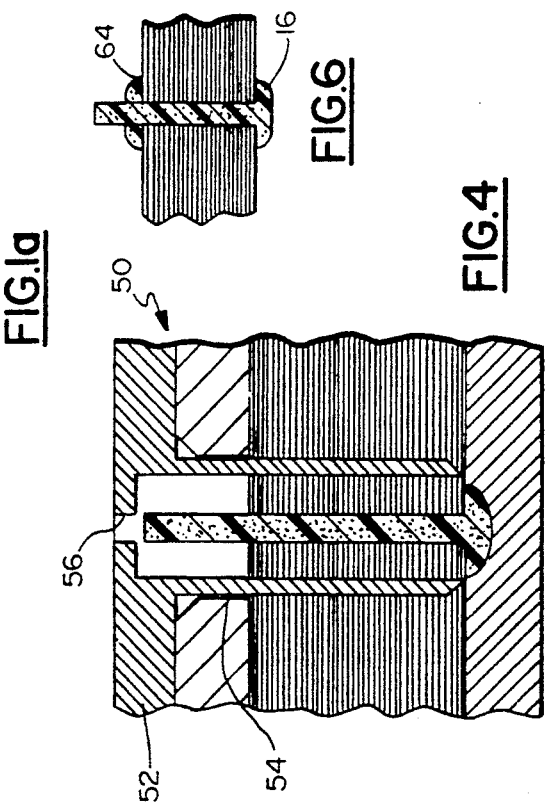

LAYERED EARPLUG

BACKGROUND OF THE INVENTION

This invention relates to the protection of the auditory canal from unwanted noise, fluids and other substances whose intrusion into the ear canal is undesirable. More specifically, this invention relates to a layered earplug for insertion in the ear canal of a person to protect the ears against undesired noise and/or fluids.

PRIOR ART

For many years now, various types of earplugs have been available to protect a user from noise and/or entrance of water into the auditory canal. A large number of patents have been granted over the years for various types of specific earplug constructions, but no one has been able to devise a truly universally acceptable earplug. The basic problem and the main difficulty in devising a satisfactory earplug is the difficulty in reconciling several conflicting requirements. The main requirements for any earplug are that they fit in the ear canal tightly so as to provide high sound attenuation and/or a water seal, while still being comfortable and hygienic for the user. Also, it is necessary that earplugs be easily installed and that they do not become loose and fall out of the ear canal of the user as the user is performing customary tasks or activities.

Since the ear canal is very sensitive, this requirement for a tight fit may lead to a feeling of pain. The shape of the outer part of an earplug is critical to the task of protecting the ear with comfort. Various earplugs of different shapes have been tried. Convoluted, conical, cylindrical, flanged, expandable and even an outer sealing cover for closing the entrance to the auditory canal of the ear of the human body are known in the art.

Generally speaking, earplugs consisting of a sufficiently soft elastic material so as not to cause discomfort to the user have had relatively low sound attenuation. Earplugs made of somewhat harder materials have a higher sound attenuation factor, but tend to be harder to fit and are more uncomfortable. Malleable or partially malleable earplugs seem to reconcile comfort with satisfactory sound attenuation, but their relatively tight fit needed to provide the sound attenuation tends to deteriorate and be lost during speaking or chewing or other physical activities, and also the necessity for custom molding of malleable type earplugs before they can be successfully introduced into the ear canal introduces a hygiene problem. Unless the hands are washed immediately before molding the earplugs and the earplugs have been thoroughly sanitized, various harmful bacteria, viruses and so forth may be introduced into the ear by the molding and insertion process. Earplugs, generally available on the market today usually consist of a foam material with various degrees of elasticity and viscosity and often soaked in a wax-type compound. When the elasticity and viscosity is high, the earplugs become partially malleable. All of these plugs are subject to one or more of the foregoing shortcomings.

OBJECTS AND SUMMARY OF THE INVENTION

Accordingly, it is an object of the present invention to provide earplugs that overcome the shortcomings of the prior art.

It is another object of the present invention to provide an earplug that can be easily and quickly inserted into the ear canal, and that will stay in place, and will be comfortable to the wearer.

It is a further object of the present invention to provide a novel layered earplug construction that can be easily secured in the ear canal in a fashion such that it will not be dislodged by ordinary talking, chewing, eating, or the like.

It is yet another object of the present invention to provide a rounded nose, cylindrical earplug that can be easily and quickly installed in the ear canals of most users which will remain securely in place and comfortable after extended periods of use.

It is a still further object of the present invention to provide an earplug that provides multiple layers of acoustic attenuation in a flexible, easily inserted form that will not accidentally fall out.

It is a still further object of the present invention to provide an earplug that will comfortably provide multiple protection against undesired intrusions into the ear canal.

In a preferred embodiment of the present invention, this is accomplished by providing a stack of thin, flexible discs bonded together in the center about a central hole and loose at the edges. The central hole is filled with sound attenuation material that also serves as a bumper and handle to insert and remove the earplug.

BRIEF DESCRIPTION OF THE DRAWINGS

Further objects of the invention, together with additional features contributing thereto and advantages accruing therefrom will be apparent from the following description of a preferred embodiment of the invention, which is shown in the accompanying drawings wherein:

FIG. 1 is a cross sectional view of an earplug according to the present invention;

FIG. 1a is a cross-sectional view taken on line 1a—1a of FIG. 1;

FIG. 2 is a cross sectional view of the first step in the formation of an earplug according to the present invention;

FIG. 3 is a view similar to FIG. 2 of the next step in the formation of an earplug according to the present invention;

FIG. 4 is a cross sectional view of the final step in the formation of an earplug according to the present invention, and FIG. 5 is a sectional view of an earplug according to the present invention, applied to a stethoscope type ear tube.

FIG. 6 is a view similar to FIG. 1 of another embodiment of the present invention.

DETAILED DESCRIPTION OF A PREFERRED EMBODIMENT

Referring now to FIG. 1, the earplug 10 of the present invention comprises a stack 11 of individual flexible discs 12, each having a hole 20 in the center thereof and each disc being bonded to the next disc about the circumference of the center hole along the core member 14. The discs 12 are stacked and then bonded together about the central hole 20 to form a bore 21 into which the core 14 is inserted. The core 14 resembles a round head rivet and is made of an acoustic attenuation material such as foam or other desirable soft material which forms not only an acoustic baffle or seal for the bore 21 of the stack of discs 12, but also acts at its lower cap end 16 as a blunt cushion so as to protect the ear during earplug insertion. At the other end there is formed a handle portion 18 for ease of insertion and removal of the earplug in the ear canal. The individual discs 12, while being bonded together about the core 14, at the center, are loose at the edges so that each individual disc can be flexed separately, as desired.

The discs 12 can be made from any suitable flexible material such as plastic, cloth, or other material that allows the free edges to be flexed and bent as the plug is inserted in the ear and which then act as anchors for the plug within the ear canal. If a smooth surface plastic material, such as polyethylene or polypropylene is used for the discs, the smooth surface facilitates the sliding of the earplug into the ear canal, since the surface friction is significantly reduced. The smoothness of the surface of the discs 12 does not appear to interfere with the secure retention of the plug in the ear canal, as will be described in detail further herein. Other materials can be used, of course, including a sheet rubber material or foam rubber, provided the foam rubber has a closed cell structure, or at least one surface of the foam is closed so as to provide the necessary acoustic attenuation of sound passing into the ear canal.

In use, the earplug 10 is grasped by the handle 18 and is inserted into the ear canal. Each individual disc 12 will flex, as will the whole stack on early insertion, and then as the stack reaches its fully inserted position, the various discs 12 will resiliently bend or conform to the shape of the ear canal and will have the edges of the discs 12 form a frictional contact with the inner ear canal surface to retain the plug in position until deliberately removed. The individual discs 12 being bonded along the central hole at the core 14 function as multiple barriers for acoustic energy and fluids attempting to penetrate into the ear canal. The core material 14 being foam or other suitable attenuation material will prevent transmission of acoustic energy/fluids through the bore of the earplug so that good acoustic attenuation and fluid seal are obtained by use of the present invention earplug. The nose 16 of the core 14 serves as a bumper and guide for the insertion of the earplug 10, as it nears the bottom of the ear canal. The nose 16 not only helps guide the earplug into the ear canal, but also will prevent undue pressure being placed against the sensitive areas of the ear canal that otherwise might be subjected to undue stress.

Each individual disc 12 being of thin plastic, or other material and easily deformed and flexed applies minimum pressure to the internal walls of the ear canal and yet, the discs in aggregate will offer acoustic attenuation and stop fluids, such as water, so that undesired acoustic noise and other substances are effectively excluded from the ear canal.

The bonding of the individual discs 12 around the central hole 20 along the core 14 can be controlled to provide a greater or lesser degree of longitudinal earplug flexibility by increasing or decreasing the extent of the bonding around the central hole 20. This bonding may be accomplished by cementing the layers together about the circumference of holes 20, or it can be accomplished by a heat penetrating tool, such as shown in FIG. 2, which is adapted to "burn" a hole in the layers of the stack 11 as it descends therethrough and simultaneously "weld" the edges of the formed hole together.

Referring now to FIG. 2, there is shown a method of making the earplug of FIG. 1 in which a number of sheets of disc material 11 are stacked up to the desired height and clamped between a base plate 24 and a top holding plate 26 to securely hold the disc sheet material 11. A heating element 30 is mounted in an insulating ring 31 positioned in the plate 28, and the power connected to the leads 34 and 36 as is well known in the art. The plate 28 is then gradually lowered allowing the tip of the heating element 30 to melt and cut away the material 11 in the stack to form the central hole 20 and bore for the earplug of FIG. 1. The heat of element 30 simultaneously seals together the adjacent edges of the central holes 20 formed inn what will become the disc members of the ear plug. A recess 32 is provided in the base plate 24 to allow the heating element 30 t penetrate all the way through the stack of disc material 11. After the heating element 30 has been allowed to penetrate all the way through the stack of disc material 11, it is withdrawn by raising plate 28 and replaced with a die insert 40, which is lowered onto the top holding plate 26 and which carries at the center thereof, in a T-shaped configuration, a nose portion 42 which mates with the top of the hole formed in FIG. 2 in the stack of disc material 11. A shearing plate 46 is positioned on top of the insert 40 and liquid foam material such as polyurethane foam is injected through a hole 44 in the shearing plate into the cavity formed by the insert 40 and the bore 20 in the stack of disc material 11. Since the bottom base plate 24 has the recess 32 formed therein, when foam material is injected through the hole 44, it fills the entire bore 20 and the recess 32 to form the central core 14 of the earplug of FIG. 1. Excess length of the core 14 is sheared off by moving the shear plate 46 sideways in FIG. 3 until the excess foam material is sheared clean.

The next step in the manufacture of the earplug shown in FIG. 4 is to remove the insert 40 and shear plate 46 from the clamped stack of disc material 11. A punch 50, which has a heavy top plate portion 52 and an elongated hole punch portion 54 which is long enough to pierce through the entire height of the stack of disc material 11 is then positioned within the hole 27 of top plate 26. The punch 54 is sized to have an I.D. equal to the desired O.D. of the earplug and fits just inside the hole 27 of the top plate 26. As punch 54 is driven through the stack of disc material 11, it will form a stack of discs 12 already bonded together around the holes 20 along the bore 21. With the core previously filled with foam in FIG. 3, this step forms a complete earplug 10.

The final step is to remove the base plate 24 and to remove the earplug 10 from the center of the punch 50 by applying compressed air or other gas to the small hole 56 in the top of the punch 50. There is thus produced, as the last operation from FIG. 4 the earplug as shown in FIG. 1.

Referring now to FIG. 5, there is shown an ear tube for a stethoscope-type hearing instrument with the earplug of the present invention applied thereto. As will be seen, in FIG. 5 the earplug 10' includes a stack of discs 12 made with the central core step of FIG. 3 omitted. The "plug" 10' is slipped over the end of the ear tube 60 after the discs 12 have been bonded together about the circumference of the central hole throughout the bore 21. If desired, a suitable protective annular pillow or cushion 62 similar to the cap 16 can be applied about the circumference of the bore 21 on one end which would be the end inserted into the ear canal of the user of the stethoscope type instrument while the other end is slipped over the ear tube 60. For use as an earplug, the bore 21 must be closed to the passage of acoustic energy or water or the like.

An alternative method for forming the discs 12 from that shown in FIGS. 2-4 is that of punching a series of discs with central holes from one or more sheets in a multiple punch and die operation and then gluing each disc 12 to the next disc 12 by applying a small amount of cement about the circumference of the central hole, so as to form the solid bore 20' of a stack of desired height. Various other methods can be used to form the earplug of the present invention. FIG. 6 is a still further embodiment in which the bonding of discs 12 is entirely omitted, and the discs are simply held under moderate pressure between the cap 16 and an added top cap 64 constituting an enlargement of the core 14. In an added step of manufacture, the stack of discs can be soaked in wax-like material to improve the seal in the ear canal and further increase sound attenuation.

While this invention has been explained with reference to the structure disclosed herein, it is not confined to the details as set forth and this application is intended to cover any modifications and changes as may come within the scope of the following claims.

What is claimed is:

1. An earplug for insertion into the exterior opening of the auditory canal of a person to prevent undesired intrusions into the canal which comprises:
    a plurality of thin, flexible, discs stacked one on top of another to form a body portion;
    a hole pierced in each disc forming a bore along a longitudinal axis of the body portion;
    bonding means securing the edges of the holes pierced in said discs to one another throughout the bore of the stack of discs;
    auxiliary barrier means inserted in the bonded bore in the stack of discs for preventing undesired sound or fluid from penetrating into the auditory can through the bore.

2. An earplug according to claim 1 wherein said auxiliary barrier means comprises an elongated rivet-like member having a round head at one end inserted in the bore, said member being formed of a foam material with the head abutted against one end of the stack discs.

3. An earplug according to claim 2 wherein said auxiliary barrier means includes an enlarged second round head member formed on said rivet-like member at the end opposite the rivet head end to securely hold the plurality of stacked discs together.

4. The earplug according to claim 2 further including said round head of the rivet-like member being positioned at the end of the ear plug to be inserted into the ear of a user and the rivet extending outwardly from the other earplug end to form a tab for inserting and removing the earplug from an ear of a user.

5. An earplug according to claim 1 wherein said auxiliary barrier means comprises an ear tube from an audio listening device.

6. An earplug according to claim 1 wherein said bonding means comprises an adhesive for joining adjacent discs together around the bore of the stack.

7. An earplug according to claim 1 wherein said discs are bonded together adjacent to the hole by thermal fusion of the discs to each other throughout the length of the bore formed in said body portion.

8. The earplug of claim 1 wherein at least one surface of said discs is a smooth, low sliding-resistance surface so that said ear plug may be easily inserted with minimal frictional resistance.

9. The earplug according to claim 8 wherein said discs are smooth polyethylene.

10. The method of forming an earplug which comprises the steps of:
    piling up a plurality of thin flexible discs to form a stack;
    compressing said stack of discs a predetermined amount;
    piercing a hole through a longitudinal axis of said stack of discs;
    binding the circumference of the pierced holes in said stack of discs together to form a bore; and
    filling the hole in said stack of discs with a barrier material.

11. The method according to claim 10 further including varying the compressing of the stack of discs to vary the flexibility of the stack of discs so that said stack may be readily inserted in an ear of a user and held therein.

12. The method according to claim 10 further including forming said stack of discs into a cylindraform body having a substantially solid center and flexible edges.

13. The method according to claim 10 further including forming said stack of thin flexible discs from sound attenuating material to provide a desired amount of sound attenuation for a user.

14. The method according to claim 10 further including forming said stack of thin flexible discs from a fluid sealing material so that upon insertion in the auditory canal of a user, undesired fluid is sealed from entry therein.

15. The method of forming an earplug comprising the steps of:
    piling up a plurality of thin flexible circular discs to form a cylindrical stack;
    compressing said stack of discs a predetermined amount of compression;
    piercing a hole through said cylindrical stack of circular discs along the axis thereof;
    filling the hole in said stack with a barrier material;
    forming a cap member at each end of said barrier material to hold said compressed stack of discs in said predetermined amount of compression.

16. An earplug according to claim 1 wherein said thin flexible discs are circular forming a cylindrical body.

17. An earplug according to claim 16 wherein said hole pierced in each disc is a circular hole forming a cylindrical bore in said stack of circular discs.

18. An earplug according to claim 10 including forming said flexible discs in circular configuration to form a cylindrical stack.

19. An earplug for use on the tip of an ear tube of a stethoscope or audio headset to prevent undesired intrusions into the auditory canal of a user which comprises:
    a plurality of thin, flexible, discs stacked one on top of another to form a body portion;
    a hole pierced in each disc forming a bore along a longitudinal axis of the body portion;
    bonding means securing the edges of the holes pierced in said discs to one another throughout the bore of the stack of discs; and
    said bore being sized to receive therein the ear tube of the stethoscope or audio headset to form auxiliary barrier means in the bonded bore in the stack of discs for preventing undesired sound or fluid from penetrating into the auditory canal of the user through the bore.

* * * * *